United States Patent [19]

Frank

[11] Patent Number: 5,423,741
[45] Date of Patent: Jun. 13, 1995

[54] APPARATUS AND METHOD FOR THE INSUFFLATION OF GAS INTO A BODY CAVITY

[75] Inventor: Milton Frank, Riverdale, N.Y.

[73] Assignee: BEI Medical Sytems, Inc., Hackensack, N.J.

[21] Appl. No.: 69,017

[22] Filed: May 28, 1993

[51] Int. Cl.⁶ .............................. A61M 13/00
[52] U.S. Cl. ............................... 604/26; 604/23
[58] Field of Search ................... 604/23-26; 128/747, 748, 204.21, 204.26

[56] References Cited

U.S. PATENT DOCUMENTS

| | | | |
|---|---|---|---|
| 3,982,533 | 9/1976 | Wiest | 604/26 |
| 4,207,887 | 6/1980 | Hiltebrandt et al. | 604/26 |
| 4,215,681 | 8/1980 | Zalkin et al. | 128/204.21 |
| 4,676,774 | 6/1987 | Semm et al. | 604/26 |
| 4,966,578 | 10/1990 | Baier et al. | 604/26 |
| 5,013,294 | 5/1991 | Baier | 604/26 |
| 5,152,745 | 10/1992 | Steiner et al. | 604/26 |

Primary Examiner—C. Fred Rosenbaum
Assistant Examiner—Adam J. Cermak
Attorney, Agent, or Firm—Malina & Wolson

[57] ABSTRACT

A device is provided for controlling flow and pressure of a gas for insufflating the abdomen during laparoscopic surgery. Compressed gas from a tank passes through the device and is stepped down through multiple stages to a pressure under 25 psi. The resultant average pressure is then reduced to a desired pressure by passing the gas through a solenoid valve and manifold in a pulsating manner. Pressure and flow are constantly monitored with signals being sent to a microprocessor which adjusts the pulse width of the gas supply to compensate for any changes in pressure.

5 Claims, 1 Drawing Sheet

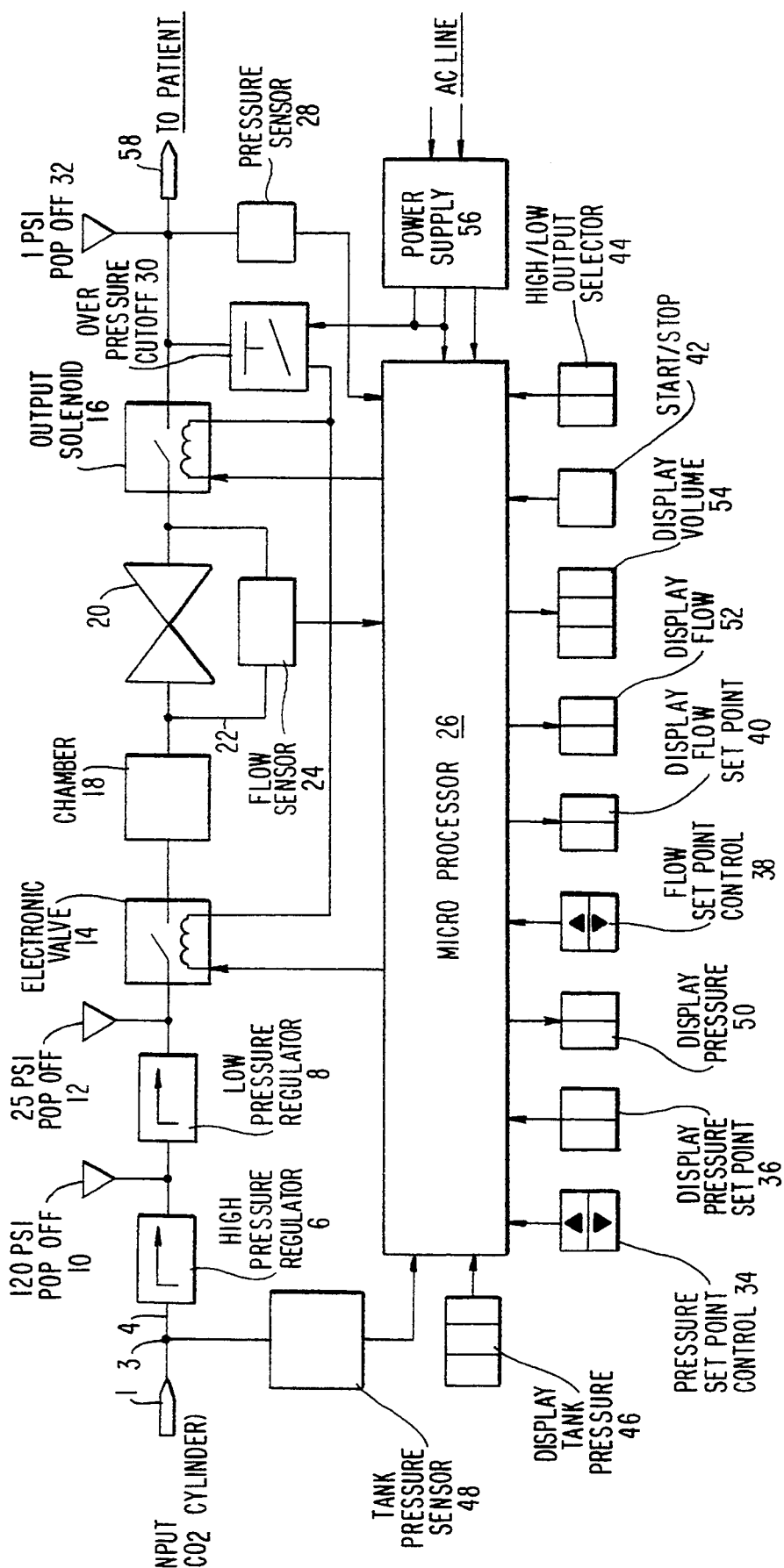

APPARATUS AND METHOD FOR THE INSUFFLATION OF GAS INTO A BODY CAVITY

BACKGROUND OF THE INVENTION

1. Field of the Invention

The invention relates to an apparatus and method for the insufflation of a gas into a body cavity with emphasis upon controlling and measuring pressure and flow rate.

2. The Related Art

An insufflator is a device utilized for introducing a gas into the abdomen during a surgical procedure to facilitate visualization. Insufflated gases such as carbon dioxide separate tissues and organs in the body. Since the gas has a lower density than the surrounding body tissues and organs, they are delineated on X-rays. Body organs, cavities and intestines are thereby better visualized in radiography.

Historically, insufflators have been utilized for diagnostic and sterilization (low-flow) laparoscopic procedures. More recently, laparoscopic procedures have been applied to more complicated operations lasting for several hours and requiring higher flow capabilities. In these more complex operations, several trocar cannulas and suction devices for removing laser or ESU smoke are usually employed. Gas loss from the abdomen increases as a result of these further inserted devices. Insufflators are therefore required which can deliver high flow rates and maintain pressure without leakage and without impairing safety.

Over the years, there have been improvements reported on insufflation technology. U.S. Pat. No. 3,858,572 (Binard et al.) describes a device including a flexible gas reservoir and a balloon for automatically releasing gas from the reservoir to the atmosphere when a predetermined pressure is exceeded. Over inflation is thereby prevented. The system further includes a syringe for selecting the volume of gas to be introduced into the abdomen.

U.S. Pat. No. 4,464,169 (Sem) describes a single hollow needle utilized for intermittently insufflating gas into the body cavity. Thereafter gas flow is interrupted while the needle is connected with a pressure measuring meter to determine both static and dynamic fluid pressure of the body cavity. Use of the needle insures that the measured pressure is correct because any blood clots and/or tissue will have been blown into the body cavity by the gas during insufflation. The conduit leading to the needle can be split into several branches to allow gas at different pressures and/or volumes to be varied.

U.S. Pat. No. 4,670,006 (Sinnett et al.) reports a fluid infusion device that includes a regulator, driven by a reversible electric motor, for regulating air pressure and flow. The regulator includes a disposable air delivery unit consisting of a filter and a tube removably connected to an air outlet controlled by a normally closed, solenoid-operated infusion valve. Separate pressure transducers detect pressure at various points in the system.

U.S. Pat. No. 4,874,362 (Wiest et al.) describes an insufflation system consisting of pressure reducer, flow meter, pressure meter and lodging control circuit. The device is without noise-generating magnetic valve, and the intra-abdominal pressure can be continuously measured without elaborate switch overs. In this device, the apparatus pressure is varied so that the nominal pressure is more rapidly reached and sudden gas losses can be better accommodated.

U.S. Pat. No. 4,966,578 (Baier et al.) discloses an insufflation system having one measuring transducer detecting dynamic pressure of the gas flow and static intra-abdominal pressure. The system adjusts for electrical changes caused, for example, by entry of a new instrument into the body cavity or a retrocession of flow resulting from differences between inlet and outlet pressures or kinking of a hose.

Most recently, U.S. Pat. No. 5,152,745 (Steiner et al.) reported an insufflator allowing the pressure in the body cavity to be measured without ever reducing the gas flow to zero. An intermediate vessel is bled with its inlet valve closed and outlet valve open. Extrapolation from the pressure decrease then allows identification of the time the pre-set pressure is reached. When an extrapolation calculation indicates a pressure short of that desired, further pumping is continued and the measuring/extrapolation cycle repeated.

The problem with many of the known systems is that they require intricate control valves to control pressure. Since these valves are motor driven, response times are slow. Systems where pressure is controlled with a diaphragm require a linear magnetic device to move the diaphragm; this combination is extremely expensive.

A still further problem with known methods is that they are limited in flow by the low operating pressures required for safety.

Accordingly, it is an object of the present invention to provide an apparatus and method for insufflating a gas into a body cavity which utilize relatively inexpensive valves in a manner that still achieves the rapid adjustment of a gas pressure system.

A further object of the present invention is to provide an apparatus and method for insufflating a gas into a body cavity that can achieve relatively high pressures and flows while nevertheless insuring a high level of safety.

A still further object of the present invention is to provide an apparatus and method for insufflating a gas into a body cavity which is electronically controlled for increased precision, accuracy, and repeatability.

A still further object of the present invention is to provide an apparatus and method for insufflating a gas into a body cavity which achieves adequate gas flow-rates and pressures for all laparoscopic procedures, including procedures with suction of smoke created by laser or electrosurgical treatments.

A still further object of the present invention is to provide an apparatus and method for insufflating a gas into a body cavity which includes self-diagnostics performed to assure unit readiness each time the unit is powered.

A still further object of the present invention is to provide an apparatus and method for insufflating a gas into a body cavity which achieves continuous monitoring of gas circuit pressure and flow-rate and which immediately disables output gas flow when a fault is detected.

A still further object of the present invention is to provide an apparatus and method for insufflating a gas into a body cavity which compensates for over-pressure transients which may be caused by trocar/cannula insertion or instrument manipulation.

These and other objects of the present invention will become more readily apparent through consideration of

SUMMARY OF THE INVENTION

Now there has been discovered an insufflator for controlling and measuring both flow and pressure of gas used to insufflate the abdomen during laparoscopic surgery. Compressed gas from a tank is introduced to the insufflator and stepped down through multiple stages to a low pressure under 25 psi. By utilization of at least one fast solenoid valve, the gas is directed through a manifold in short pulses, thereby reducing the average pressure to the desired pressure. The pressure and flow are constantly monitored with signals being sent to a programmable control device in the form of a microprocessor. The control device adjusts the gas flow to a pulse width sufficient for compensating any changes in pressure. When pressures fall below a set point, the control device attempts to compensate using the maximum flow that has been pre-set. In this mode (pressure not being maintained), the device serves as a flow control. Pulse width modulation serves as the primary mechanism to control pressure/flow and allows achievement of the various objects of the invention.

Accordingly, the invention provides an insufflator for controlling and measuring pressure of a gaseous fluid introduced into a living body cavity comprising:

a main flow line with a coupling mechanism at a terminal end for receiving the fluid at an initial input pressure;

a high pressure regulator downstream from the coupling mechanism for reducing the initial input pressure to a lower first pressure;

a low pressure regulator downstream from the high pressure regulator for reducing the first pressure to a lower second pressure;

a first valve downstream from the low pressure regulator, the valve being electronically actuated to open and close in a pulsating manner to reduce the second pressure to a lower third pressure;

a pressure sensor downstream from the first valve to measure a downstream pressure and transmit a signal representative of the downstream pressure; and a programmable control device for receiving the signal and regulating actuation of the first valve based on the signal and a pre-programmed set-pressure.

The insufflator may further include a second valve electronically operated to open and close in pulsating manner pursuant to regulation by the programmable control device. This second valve will be downstream from the first valve. An expansion chamber as well as a manifold can be positioned between the first and second valve. A flow sensor branched from the main flow line can be utilized to flow across the manifold. Flow measurements are converted to an electronic signal and transmitted from the sensor to the programmable control device.

Furthermore, an over-pressure cutoff can be inserted downstream from the second valve. Upon sensing of a pressure higher than a pre-set value, the over-pressure cutoff can communicate with the first and second valve to shutdown flow. The over-pressure cutoff is best positioned upstream from the pressure sensor.

According to the invention there is also provided a method for insufflating a living body cavity comprising:

charging a gas such as carbon dioxide at an initial input pressure from a compressed cylinder source into a main flow line of an insufflator device;

reducing step-wise the initial input pressure by passage of the gas through a high—and then a low—pressure regulator to obtain consecutively lower first and second pressures, respectively; and pulsatingly modulating the second pressure via an electronically operated valve, pulsations of the valve being regulated by a programmable control device receiving input from a pressure sensor downstream from the valve.

BRIEF DESCRIPTION OF THE DRAWING

Of the above features, advantages and object of present invention will more fully be appreciated through the following detailed discussion, reference being made to the drawing which consists of a sole FIGURE illustrating in schematic form the insufflator system.

DETAILED DESCRIPTION

Medical grade liquified carbon dioxide held in cylinder is introduced into the insufflating system through a coupling mechanism in the form of a standard pen yoke 3. Gaseous carbon dioxide is then directed along the main flow line 4 into a high pressure regulator 6. Across this regulator the original 1,000 psi is brought to a level below 120 psi. The gas pressure is then further reduced to a value below 25 psi by traversal through a low pressure regulator 8. Branched from the main line are a pair of pressure relief devices 10 and 12 set to "pop off" at 120 psi and 25 psi. Device 10 is positioned between the high pressure regulator 6 and the low pressure regulator 8. Device 12 is downstream from the low pressure regulator 8.

Further downstream, the gas is directed into a first valve 14 electronically actuated to open and close in a pulsating manner. A solenoid within the valve allows a rapid modulation in an on and off sequence. The maximum pressure deliverable through the system to the body cavity can be reduced through the aforementioned modulation which provides an average pressure proportional to the on time/(on time plus off time) multiplied by the maximum available pressure.

A second valve 16, also utilizing a solenoid, is disposed along the main line 4 downstream from the first valve 14. Between valves 14 and 16 is an expansion chamber 18 and a manifold 20. Across the inlet and exit points of manifold 20 are branched flow lines 22 leading to a flow sensor 24 to measure flow rate.

Control of the insufflator is achieved through a programmable control device 26 consisting of an electronics package with a microprocessor logic. The first and second valves 14 and 16 are electronically controlled by the logic of microprocessor 26 based upon input from flow sensor 24 and a pressure sensor 28, the latter being branched from mainline 4 downstream from valve 16.

An over-pressure cutoff mechanism in the form of a transducer 30 branches from the main flow line 4 at a point downstream of the valve 16. Under excess pressure the cutoff mechanism is actuated and electronic signals sent simultaneously to the upstream pulsating valves 14 and 16 causing these to shutdown flow. Downstream from over-pressure cutoff 30 is a further pressure relief valve 32 set to "pop off" if pressure is in excess of 1 psi.

Subsequent to passage across the aforementioned devices, valves and mechanisms, the gas is directed into the abdomen of a patient undergoing diagnostic treatment or surgery. The programmable control device 26 carries a series of button actuated functions with respective display windows. These include a pressure set point control 34 in conjunction with a pressure set point display 36, a flow set point control 38 with a respective flow set point display 40, a start/stop function 42 and a high/low output selector 44. There also is a tank pressure display 46 which reports the signal from the carbon dioxide tank pressure sensor 48 upstream from regulator 6. Additionally there are a series of output displays which include a pressure display 50, a flow display 52 and a volume display 54. Power is supplied to the programmable control device 26 through a supply 56 which also actuates over-pressure cutoff 30.

Operation of the system begins by actuation of the power supply 56. Microprocessor 26 will then automatically perform a self-diagnostic test routine. Digital displays 36, 40, 44, 46, 50, 52, and 54 will become illuminated. The valve controlling the high pressure gas supply tank 1 is then opened; tank pressure will be measured by sensor 48, and a proportional signal is sent to microprocessor 26 which in turn is recorded on tank pressure display 46. Carbon dioxide pressure is then reduced and gas flows consecutively through the high pressure regulator 6 and low pressure regulator 8. Thereafter, the carbon dioxide is pulsatingly modulated through valve 14 by control commands for "on"-"off" signals from microprocessor 26. The set point controls selector buttons 34 and 38 for control of pressure and flow can be operated to change the respective output pressure and flow set-points. Digital displays 36 and 40 confirm these changes. Actual measurements of pressure and flow are reported through displays 50 and 52. These actual values of flow derive from the flow sensor 24 measurement and pressure sensor 28 measurement fed back into microprocessor 26.

When the insufflator system has been primed as described above, a Veress Needle or other peritoneal entry device can be inserted into the patient. Placement of the Veress Needle must be confirmed by the standard Aspiration Test and also the Hanging Drop Test. Connector 58 in the form of a Luer lock at the terminus main flow line 4 can then be connected to the Veress Needle. Carbon dioxide which has passed through the insufflator can then be delivered to the patient through the Veress Needle.

The foregoing description illustrates only selected embodiments of the present invention. In light thereof, various modifications will be suggested to one skilled in the art, all of which are within the spirit purview of this invention.

What is claimed is:

1. An insufflator for controlling and measuring the pressure of a gaseous fluid introduced into a living body cavity comprising:

a main flow line with a coupling means at a terminal end thereof for receiving said fluid at an initial input pressure;

a high pressure regulator downstream from said coupling means for reducing said initial input pressure to a lower first pressure;

a low pressure regulator downstream from said high pressure regulator for reducing said first pressure to a lower second pressure;

a first valve downstream from said low pressure regulator;

a means for electronically actuating said first valve to open and close in a pulsating manner to reduce said second pressure to a lower third pressure;

a pressure sensor downstream from said first valve to measure a downstream pressure and transmit a signal representative of said downstream pressure;

a programmable control means for receiving said signal and regulating actuation of said first valve based on said signal and a pre-programmed set-pressure;

a second valve downstream from said first valve;

a means for electronically actuating said second valve to open and close in a pulsating manner pursuant to regulation by said programmable control means; an expansion chamber and a manifold between said first and second valve; and a flow sensor branched from said main flow line to measure flow across said manifold, said sensor transmitting a signal based on a sensed flow to said programmable control means.

2. An insufflator according to claim 1 further comprising an over-pressure cutoff downstream from said second valve and communicating with said first and second valve to shut down flow upon sensing of a pressure greater than a pre-set value.

3. An insufflator according to claim 2 wherein said pressure sensor is downstream from said over-pressure cutoff.

4. An insufflator according to claim 1 wherein said first valve includes a solenoid which is opened and closed in said pulsating manner.

5. A method for controlling and measuring the pressure of a gaseous fluid introduced into insufflating a living body cavity comprising:

providing an insufflator having a structure comprising:

a main flow line with a coupling means at a terminal end thereof for receiving said fluid at an initial input pressure;

a high pressure regulator downstream from said coupling means for reducing said initial input pressure to a lower first pressure;

a low pressure regulator downstream from said high pressure regulator for reducing said first pressure to a lower second pressure;

a first valve downstream from said low pressure regulator;

a means for electronically actuating said first valve to open and close in a pulsating manner to reduce said second pressure to a lower third pressure;

a pressure sensor downstream from said first valve to measure a downstream pressure and transmit a signal representative of said downstream pressure;

a programmable control means for receiving said signal and regulating actuation of said first valve based on said signal and a pre-programmed set-pressure;

a second valve downstream from said first valve;

a means for electronically actuating said second valve to open and close in a pulsating manner pursuant to regulation by said programmable control means;

an expansion chamber and a manifold between said first and second valve; and a flow sensor branched from said main flow line to measure flow across said manifold, said sensor transmitting a signal based on a sensed flow to said programmable control means;

charging said gaseous fluid at said initial input pressure from a compressed cylinder source into said main flow line of said insufflator;

reducing said initial input pressure by passage of said gaseous fluid through said high-pressure and then through said low-pressure regulator to obtain consecutively lower first and second pressures pulsatingly modulating said gaseous fluid having said second pressure via said means for electronically actuating said second valve, pulsations of said valve being regulated by said programmable control means receiving input from said pressure sensor downstream from said first valve; and introducing said pulsating gaseous fluid body cavity.

* * * * *